United States Patent [19]

Saldivar, Jr. et al.

[11] Patent Number: 5,401,639

[45] Date of Patent: Mar. 28, 1995

[54] STABILIZED BILIRUBIN CALIBRATOR SOLUTION AND METHOD THEREFOR

[75] Inventors: Louis Saldivar, Jr., Kenosha; Barbara J. England, Milwaukee, both of Wis.

[73] Assignee: Abbott Laboratories, Abbott Park, Ill.

[21] Appl. No.: 935,677

[22] Filed: Aug. 25, 1992

Related U.S. Application Data

[63] Continuation of Ser. No. 600,797, Oct. 22, 1990, abandoned.

[51] Int. Cl.$^6$ .................. C12Q 1/54; G01N 33/00
[52] U.S. Cl. ......................... 435/14; 435/801; 436/97
[58] Field of Search .............. 435/14, 801; 436/97; 514/21

[56] References Cited

U.S. PATENT DOCUMENTS

| | | | |
|---|---|---|---|
| 4,144,306 | 3/1979 | Figueras | 422/56 |
| 4,414,334 | 11/1983 | Hitzman | 435/262 |
| 4,476,224 | 10/1984 | Adler | 435/253.6 |
| 4,775,626 | 10/1988 | Armenta | 435/244 |
| 5,047,395 | 9/1991 | Wu | 514/2 |

OTHER PUBLICATIONS

"Properties Of The Oxyrase TM Enzyme System"; Technical Bulletin TB 890411; Oxyrase, Inc. (no date available).

*Primary Examiner*—Michael G. Wityshyn
*Assistant Examiner*—Ralph Gitomer
*Attorney, Agent, or Firm*—Lawrence S. Pope; Richard D. Schmidt

[57] ABSTRACT

A stabilized anoxic diagnostic reagent solution comprising an oxygen labile reagent, glucose oxidase, glucose, a hydrogen donor, sterile membrane fragments derived from bacteria having membranes containing an oxygen transfer system, and a reagent binding agent. The stabilized reagent has at least six months storage stability at 2°–8° C. and open vial stability of at least three weeks.

12 Claims, 2 Drawing Sheets

STABILIZED BILIRUBIN CALIBRATOR SOLUTION AND METHOD THEREFOR

This application is a continuation of application Ser. No. 07/600,797, filed on Oct. 22, 1990, now abandoned.

FIELD OF INVENTION

The present invention is directed to a stabilized anoxic diagnostic reagent solution containing an oxygen labile reagent which may be stored in a liquid form at temperatures as high as 45° C. for at least four (4) days, and permit their direct use as reference standards in instrumental analysis without the necessity for addition of water to them. In particular, the invention relates to the use of oxygen reducing enzyme systems in oxygen labile reagent solutions, especially reagent solutions used for calibrators and controls.

DESCRIPTION OF THE RELATED ART

Many materials deteriorate in the presence of oxygen. Various methods have been used to avoid the deteriorating effects of oxygen.

Biologically active substances such as found in sera, enzymes, lipids, hormones, electrolytes, and biologically active substrates or metabolites, are used widely in the diagnosis of diseases. They are used as reference standards for instrumental automated colorimetric analysis since they contain all or most of the components of the unknown to be analyzed. Once the diagnosing physician is aware of the basic concentration of components (differences vs. normal mean ranges of concentration of each components), the diagnosis can be made more objectively. In their natural form, when separated from their normal biological environment, such biologically active substances are unstable and undergo undesirable changes under the influence of heat, enzyme action, hydrolysis, oxidation and other influences causing undesirable molecular transformation therein. In the past, several methods of preservation have been utilized for such labile reagents.

One such procedure involves freeze-drying of the reagent. The freeze-drying procedure essentially involves rapidly reducing the temperature of the reagent containing solution followed by de-watering to a very substantial, if not total, extent at reduced pressure. If the reagent was additionally subjected to oxygen reduction then further procedures would be necessary. Not only is this procedure expensive, but it also requires reconstituting (resupplying) the normal water prior to use of the stored reagent. Natural proteins tend to denature upon losing substantial concentrations of water. Thus, natural proteins could undergo compositional changes and loss of biological activity due to substantial de-watering occurring in the freeze-drying. Additionally, the freeze dried reagent often presents a turbid condition after it is reconstituted with water. This can cause analytical error because many of the automated analytical procedures basically involve colorimetry. During the reconstitution procedure, volume errors are sometimes introduced when, for example, the serum is reconstituted to its original liquid form by the addition of the water to the freeze-dried concentrate.

Prior to the discovery of this invention, certain diagnostic reagents such as bilirubin have been stabilized by polyols such as ethylene glycol. However, bilirubin stabilized in this manner must be kept at −20° C. and it does not survive 45° C. stress very well. Open vial stability of these materials is about 7 days. On the other hand, freeze-drying is the most frequently used method of stabilizing bilirubin. Once reconstituted, however, these materials do not have good stability, and errors in solubilizing the desiccated bilirubin may occur. These reconstituted standards generally require about 30 minutes for reconstituting.

U.S. Pat. No. 4,414,334 to Hitzman discloses the removal of ambient oxygen from aqueous liquids, including canned foods and beverage products, which are catalyzed by an enzymatic deoxygenation system comprising alcohol oxidase in the presence of alcohol, optionally with the addition of catalase.

U.S. Pat. No. 4,476,224 to Adler teaches the use of an enzyme system to promote the growth of anaerobic bacteria. The enzyme system of Adler comprises sterile membrane fragments derived from bacteria having membranes containing an electron transfer system which reduces oxygen to water. Optionally a hydrogen donor may be added to facilitate the reduction of water.

A technical bulletin, TB890411 released by Oxyrase, Inc. entitled "Properties of the Oxyrase TM Enzyme System" discloses that the Oxyrase TM enzyme system (sterile membrane fragments) in the presence of a suitable hydrogen donor, reduces dissolved oxygen directly to water. The bulletin also teaches that the enzyme system can be incorporated into oxygen-sensitive analytes used in automated, diagnostic instruments.

U.S. Pat. No. 4,775,626 to Armenta, et al. teaches a method for reducing the oxygen content of a medium in which anaerobic cells are present. The method comprises having an effective amount of an oxidase and substrate for the oxidase in fluid contact with an aqueous medium. The medium can also contain a hydrogen peroxide scavenger.

The conversion of bilirubin through oxidation to biliverdin and other products is the main disadvantage of most bilirubin solutions. A system to prevent this oxidative process has been developed and is the invention presented here. The present invention offers a diagnostic reagent solution that is stable at 45° C. for at least four days, has at least six months of open vial stability, and the finished product is already in liquid form.

SUMMARY OF THE INVENTION

The present invention is based upon the discovery of an aqueous bilirubin solution having sufficient stability that it can be shipped and stored for at least as long as six months at a temperature of 2°–8° C. and for at least four days at 45° C., has at least three weeks of open vial stability, and the finished product is already in liquid form.

The stabilization of the reagent is achieved by using a combination of oxygen reducing enzyme systems in a synthetic matrix comprising a reagent binding agent such as albumin to prevent the oxidation of the reagent. The stabilized anoxic diagnostic reagent solution comprises an oxygen labile reagent, a reagent binding agent, a first oxygen reducing enzyme system which comprises glucose oxidase and its substrate glucose, and a second oxygen reducing enzyme system which comprises a hydrogen donor and sterile membrane fragments derived from bacteria having membranes containing an oxygen transfer system which reduces oxygen to water. The solution may also comprise catalase, however, in amounts of 150 u/ml or greater open vial stability decreases from that obtained with 50 u/ml. Additional components, such as antioxidant used as a free radical scavenger, alcohol, buffer and surfactant may also comprise the matrix. D-lactate is the preferred hydrogen donor.

Over all, in the preferred embodiment bilirubin is stabilized by removing molecular oxygen, providing free radical scavengers providing an anti-oxidant, providing a chelating agent, binding bilirubin to albumin, and providing for light protection in the final container. It is likely that several of these approaches work synergistically with the enzyme systems to bring about the stability obtained. It is known that oxygen increases photodegradation, thus by removing oxygen we also reduce photodegradation. Reducing agents and chelators also behave synergistically with anti-oxidants. The advantages obtained are greater heat stability, the product is a liquid, the product has at least three weeks open vial stability, and the product does not contain human materials, thereby making this less hazardous than many of the commercially available standards which do contain human serum.

THE DETAILED DESCRIPTION OF THE INVENTION

Figure 1:
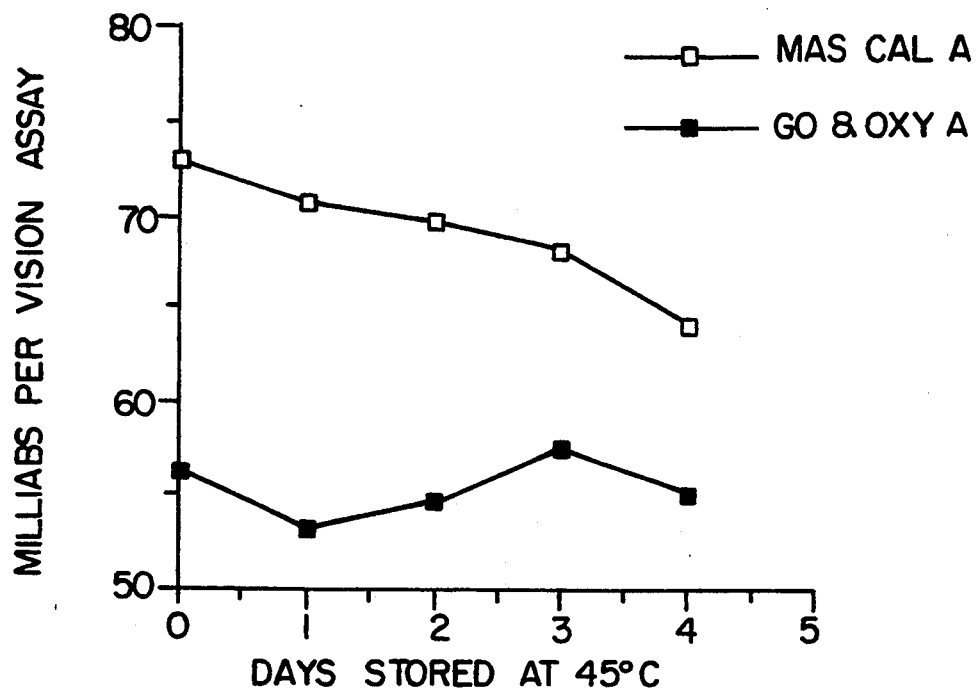
FIG. 1 is a graph comparing the activity of two bilirubin A calibrators during 45° C. heat stress testing.

As used herein, and in the appended claims, the following terms, unless otherwise indicated, have the meanings set forth herein: "percent" and "parts" refer to percent and parts by weight; g small means gram or grams; mg means milligram or milligrams; l means liter or liters; ml means milliliter or milliliters; dl means deciliter or deciliters; ul means microliter or microliters; and M means molar and equals the number of moles of a solute in one liter of a solution; mM means millimolar. All temperatures are in degree Centigrade, °C.

The present invention involves the stabilization of a diagnostic reagent solution that comprises an oxygen labile reagent, or analyte, the addition of a reagent binding agent, and at least two oxygen reducing enzyme systems. It has been discovered that by adding an oxygen labile reagent to a matrix containing a reagent binding agent and the further addition of two oxygen reducing enzyme systems to that matrix a significant increase in the high temperature stability and open vial stability of the resulting reagent solution results.

In a preferred embodiment, a stabilized bilirubin solution that has been developed for the purpose of instrumentation calibration and control is placed in a synthetic matrix. Enzyme systems are used to remove molecular oxygen. An antioxidant is used as a free radical scavenger and alcohol is used to solubilize the free radical scavenger wherein the alcohol may also be a known free radical scavenger. Albumin is used as the reagent binding agent to bind bilirubin which offers some additional stability.

The enzymatic reactions, of our invention, used for oxygen removal are as follows:

1) Glucose + Glucose oxidase + Oxygen → Gluconic acid + Hydrogen peroxide

2) Hydrogen peroxide + catalase → oxygen + water

3) Oxygen generated in step 2) recycles into step 1)

4) Membrane fragments + oxygen + hydrogen donor → pyruvate + water

Inhibition of reagent precipitation (e.g. bilirubin) is by the binding action of a reagent binding agent such as albumin, gluconic acid and possibly by a buffer system. The glucose, glucose oxidase reaction removes oxygen and prevents the formation of oxygen ($O_2$). Catalase may be used to remove hydrogen peroxide. The sterile membrane fragments, commercially available as Oxyrase, is a secondary oxygen removal system useful in the pre-reduction step of the following process.

By preventing reactive oxygen intermediates our invention should afford stability to many substances. Some substances which may have improved stability may be enzymes, reducing substances, pharmaceuticals, antibodies, antigens and substrates especially when linked to enzymes or other oxygen labile components.

EXAMPLES

The following examples, which described various modes including the best mode presently contemplated by the inventors, are presented solely for the purpose of disclosing and explaining the invention, and is not intended to be limiting.

EXAMPLE 1

The following is an example of the formulation process for producing a stabilized anoxic solution containing bilirubin as the oxygen labile reagent.

A matrix is prepared to contain the following in grams per liter.

| | | |
|---|---|---|
| a. | Ethanol | 9.5 {to solubilize BHT} |
| b. | Polyoxyethylene 23 Lauryl Ether (BRIJ 35) | 64.36 |
| c. | Bistrispropane | 30.037 |
| d. | Glucose | 5.3 |
| e. | Butylated Hydroxy Toluene (BHT) | 0.213 |
| f. | dl-lactate | 3.57 |
| g. | Bovine Serum Albumin (BSA) | 53.15 |
| h. | Gentamicin | 1.0 |
| i. | HCl | As necessary to adjust pH |
| j. | NaOH | 4 (To dissolve bilirubin powder) |

The pH is adjusted to 7.85.

Oxyrase TM enzyme system (Oxyrase, Inc., Ashland, Ohio) is added into the matrix so as to obtain 0.3 units/ml of Oxyrase. (A unit of activity reduces 1.0% of the initially dissolved oxygen in each second per milliliter under standard conditions. The standard conditions are 37° C., pH of 8.4 in a 20 mM phosphate buffer, 10 mM sodium lactate as the hydrogen donor, and an air saturated solution.) Oxyrase TM enzyme system is described in the literature and U.S. Pat. No. 4,476,224 as sterile membrane fragments derived from bacteria having membranes containing an electron transfer system (oxygen transfer) which reduces oxygen to water. Any such membrane fragments should operate similarly and could be substituted for Oxyrase TM. After the addition of the enzyme system room air must be excluded from the solution thereafter. This can be accomplished by maintaining nitrogen in the headspace.

Catalase from about 0 to about 150 units/ml can be added to remove any hydrogen peroxide which may be generated by the glucose oxidase reaction. However it has been observed that catalase in amounts more than 150 units/ml reduced open vial stability may result.

After the oxygen has been removed by the Oxyrase™ enzymatic reaction or after incubating the matrix with the Oxyrase™ enzyme system for about 60 minutes, glucose oxidase is added into the matrix so as to obtain 13 units/ml of glucose oxidase. Bilirubin dissolved in 0.1M sodium hydroxide is then added in until the proper amount for that particular solution is achieved. The bilirubin powder (Phansthiel, Inc., Waukegan, Ill.) dissolved in sodium hydroxide must not be hazy, but clear and amber colored prior to its addition to the matrix solution. The bilirubin may be conjugated, unconjugated or both.

As the following examples and data will show the following ranges for specific components added to a bilirubin calibrator solution are preferable in accordance with this invention.

1. pH—after all glucose is converted to gluconic acid (above 7.0) more preferably a pH between about 7.4 and 8.1
2. Glucose—initial glucose level 0.1% to 0.5% which yields between about 0.1 and 0.53 weight percent of gluconic acid upon the action of the glucose oxidase, excessive glucose may cause bilirubin precipitation
3. BHT—0% to about 0.024%, more preferably between about 0.0016 and 0.024 weight percent
4. Oxyrase—0.3 to about 0.6 units/ml
5. Albumin—4% to 6%
6. Catalase—0 to about 150 units/ml, excess catalase may reduce open vial stability.
7. Alcohol—about 1% more preferably between about 0.9 and 1.1 weight percent ethanol
8. A non-ionic surfactant—about 5% to about 6%
9. Glucose oxidase—10 to about 27 units/ml
10. Bilirubin—0 to about 30 mg/dl
11. Hydrogen donor—5 to about 20 mM Other ingredients may also be present. Table 1, below, shows the basic elements necessary to produce a stabilized anoxic reagent solution encompassed by our invention.

TABLE 1

| Ingredient | Amount |
| --- | --- |
| Glucose | 1–10,000 mg/dl |
| Glucose oxidase | 0.1–2 units/l |
| Binding agent | 1–10% |
| Hydrogen donor, more preferably d-lactate | 1–100 mM |
| Membrane fragment enzyme system | 0.1–1 unit/l |

EXAMPLE 2

Bilirubin calibrators, at levels of 2 mg/dl(A), 10 mg/dl(B) and 20 mg/dl(C), were prepared by the method of Example 1. A set of vials of each calibrator level was kept at 45° C. Once each day the vials were tested and bilirubin levels were determined using a Vision™ analyzer and test cards. (Abbott Laboratories, Abbott Park, Ill.) according to the manufacture's instructions.

The control calibrators were stored at 2°–8° C.

Figure 2:
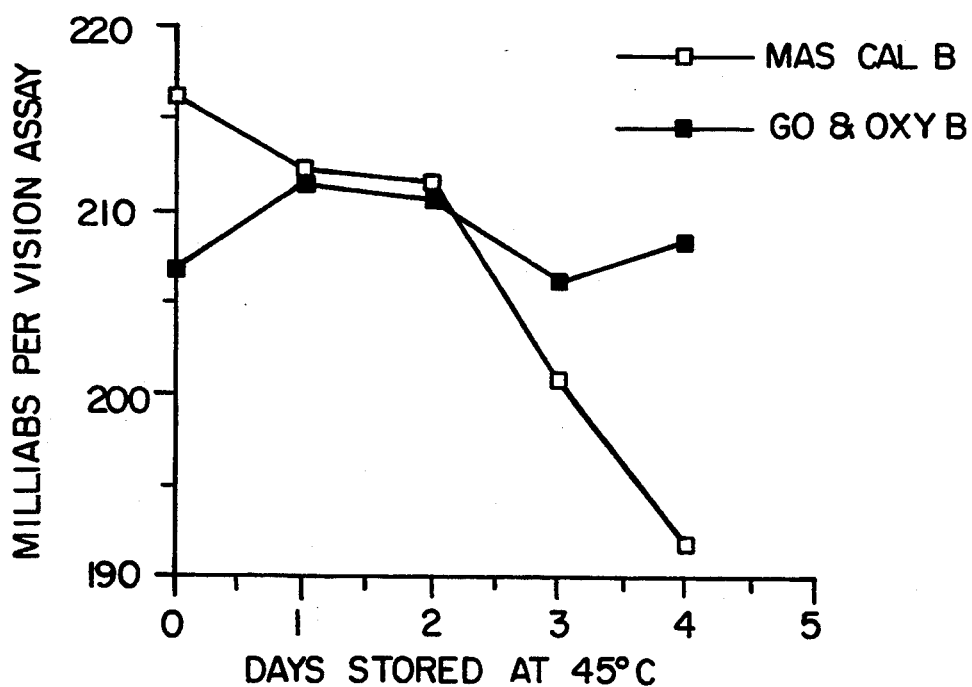
FIG. 2 is a graph comparing the activity of two bilirubin B calibrators during 45° C. heat stress testing.
Figure 3:
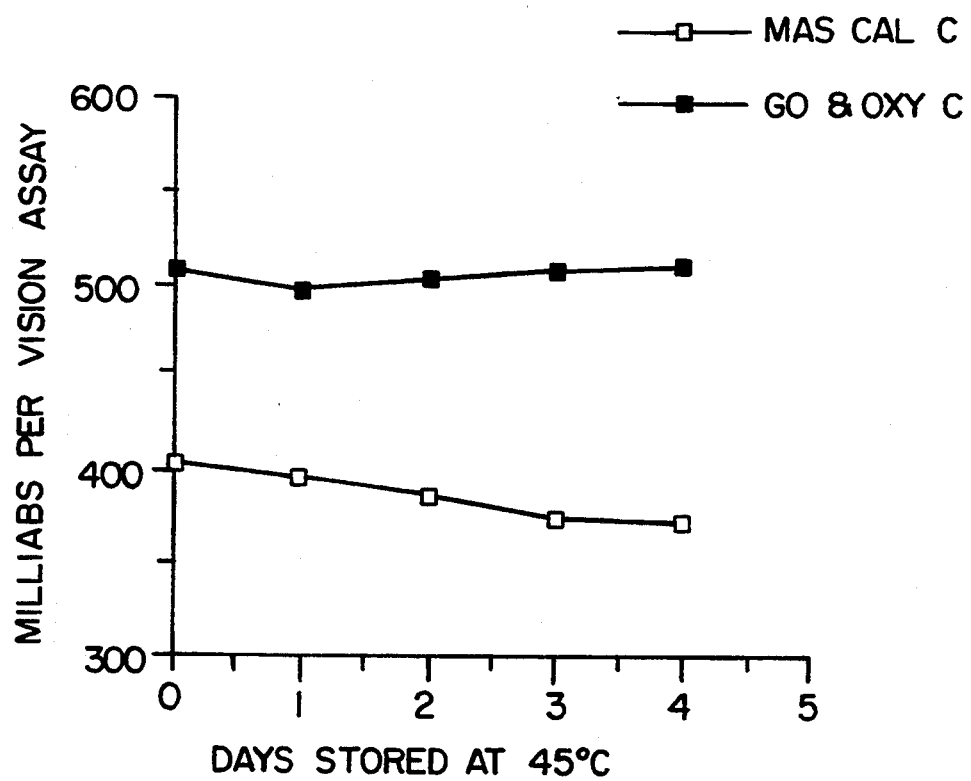
FIG. 3 is a graph comparing the activity of two bilirubin C calibrators during 45° C. heat stress testing.

FIGS. 1, 2 and 3 show the results of the above study as well as the results of a parallel test conducted on a commercially available bilirubin calibrator (Medical Analysis Systems) prepared to comparable levels. In FIGS. 1, 2 and 3 MAS CAL is the commerical calibrator and GO & OXY CAL is the calibrator of this invention. The points plotted on the graphs are average values. The calibrators prepared with the two enzyme systems of this invention showed superior stability and activity over the commercial formulation.

EXAMPLE 3

Vials of bilirubin calibrators at each of three levels (as in Example 2) were prepared as in Example 1. Table 2 shows the exact composition of the solutions and the results of the open vial study, discussed below, in days. The reagent solution was considered acceptable if it was within the following ranges when the activity was compared to the appropriate control: calibrator A 15%, calibrator B 5%, calibrator C 5%.

Three vials of each of the three calibrator levels were stored at 2°–8° C. Each work day (Monday through Friday) the vials were opened, then closed and left on a bench top for eight (8) hours. A baseline value was determined for each calibrator level by testing three vials from each level for five days prior to the commencement of this experiment. Throughout the test period bilirubin levels were obtained at random points in time.

Bilirubin values were obtained by using a Vision™ analyzer (Abbott Laboratories, Abbott Park, Ill.) and test cards according to the manufacture's instructions.

TABLE 2

| | | | |
| --- | --- | --- | --- |
| Glucose | 0.1% | 0.3% | .5% |
| Glucose Oxidase | 12.9 u/ml | 12.9 u/ml | 20 u/ml |
| Catalase | 0 | 50 u/ml | 150 u/ml |
| Oxyrase | 0.6 u/ml | 0.3 u/ml | 0.6 u/ml |
| dl Lactate | 30 mM | 30 mM | 30 mM |
| Butylated Hydroxy Toluene (BHT) | 0.02% | 0.02% | 0.02% |
| Ethanol (EtOH) | 1% | 1% | 0.95% |
| Polyoxyethylene 23 Lauryl Ether (BRIJ 35) | 6% | 5% | 6.4% |
| pH | 7.74 | 7.7 | 7.8 |
| Bistrispropane | 0.1 M | 0.1 M | 0.1 M |
| Gentamicin | 0.1% | 0.1% | 0.1% |
| BSA | 5% | 5% | 5% |
| Bilirubin | 25 mg/dl | A,B,C | 2A,2B,2C |
| Open Vial (Days) | 40 | 25 | 15 |

In our formulation the following reactions are prevented. Therefore it is probable that many products may have extended stability in the Table 1 formulation.

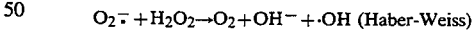

$O_2^- + H_2O_2 \rightarrow O_2 + OH^- + \cdot OH$ (Haber-Weiss)

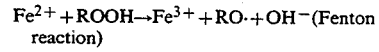

$Fe^{2+} + ROOH \rightarrow Fe^{3+} + RO \cdot + OH^-$ (Fenton reaction)

The Haber-Weiss is prevented by the removal of molecular oxygen which prevents super-oxide formation. An alternate inhibitor of the Haber-Weiss reaction is the degradation of $H_2O_2$. The Fenton reaction is inhibited by the chelation of iron.

The inhibition of these two reactions is believed to be a major source of stability in the formulation. To scavenge any preexisting free radicals BHT or BHA may also be incorporated into some formulations.

EXAMPLE 4

Many complex biological molecules such as hormones, lipids, steroids, calechols, etc. as well enzymes, reducing substances, pharmaceuticals, antibodies, antigens and substrates could have their shelf and open vial life extended by this invention. The particular substance would place limits on the substrate concentrations of Table 1 and any buffer system which may be necessary.

A stabilized anoxic solution containing an oxygen labile reagent could be prepared as in Example 1 which would comprise the substrate of Table 1. Additionally the solution could further comprise BHT or BHA from 0.001 to 0.04%, buffer such as bistrispropane with adequate strength to maintain a pH compatible with the system, a detergent and organic solvent as required for BHT micelle formation. Low levels of glucose oxidase are generally adequate since the substrate turnover is very high, however high levels may to lead greater stability. The absorbance of this yellow compound may be a limiting factor in spectral applications.

Some enzymes and organic and inorganic chemicals are stabilizing by substances that are reducing in nature. Cysteine and ascorbic acid, for example, when used in this fashion are of limited value since they are themselves subject to oxidation. In a matrix such as described in the above examples these oxygen labile substances could be stabilized so that they in turn could function as stabilizer.

In the case of enzyme reagents strong chelators may inactivate the enzyme by chelation of a metallic coenzyme. In such a case the gluconic acid generation may be limited by limiting the glucose substrate. Degassing, pre-treating with the membrane fragment enzyme system and then addition of glucose oxidase may also limit the generation of gluconic acid.

It will be appreciated by one skilled in the art that the embodiments described and the alternative embodiments presented are intended as examples rather than as limitations. Thus, the description of the invention is not intended to limit the invention to the particular embodiments disclosed, but it is intended to encompass all equivalents and subject matter within the spirit and scope of the invention as described above and as set forth in the following claims.

We claim:

1. A stabilized aqueous bilirubin calibrator solution comprising:
    between about 1.0 and 30 mg/dl of bilirubin;
    between about 0.9 and 1.1 weight percent ethanol;
    between about 5 and 6 weight percent polyoxyethylene 23 lauryl ether;
    between about 0.0016 and 0.024 weight percent butylated hydroxy toluene;
    bistrispropane at about 0.1M;
    between about 0.1 and 0.53 weight percent gluconic acid generated in situ from glucose;
    between about 4 and 6 weight percent albumin;
    d-lactate hydrogen donor at between about 3 and 20 mM; and
    between about 0.3 and 0.6 units/ml sterile membrane fragments derived from bacteria having membranes containing an oxygen transfer system which reduces oxygen to water;
    wherein said stabilized aqueous bilirubin calibrator solution has a pH from about 7.7 to about 7.85 and has a storage stability of at least six months at from about 2° to about 8° C. and at least four days at 45° C., said calibrator solution further having an open vial stability of at least three weeks at from about 2° to about 8° C.

2. The bilirubin calibrator solution of claim 1 which further comprises catalase.

3. The bilirubin calibrator solution of claim 2 wherein the catalase is present in an amount up to about 150 units/ml.

4. A method for stabilizing an aqueous bilirubin calibrator solution comprising:
    preparing a matrix containing:
    between about 0.9 and 1.1 weight percent ethanol;
    between about 5 and 6.4 weight percent polyoxyethylene 23 lauryl ether;
    bistrispropane at about 0.1M;
    between about 0.1 and 0.53 weight percent glucose;
    between about 0.0016 and 0.024 weight percent butylated hydroxy toluene;
    d-lactate hydrogen donor at between about 5 and 30 mM; and
    between about 1 and 10 weight percent albumin;
    adjusting the pH of the matrix to from about 7.7 to about 7.85;
    adding into the matrix sterile membrane fragments derived from bacteria having membranes containing an oxygen transfer system which reduces oxygen to water so as to obtain between about 0.3 and 0.6 units/ml of activity and thereafter excluding air from contacting said matrix;
    adding to the air excluded matrix catalase in an amount up to about 150 units/ml;
    after oxygen is removed from said matrix by the oxygen transfer system, adding into said matrix sufficient glucose oxidase to obtain between about 10 and 27 units/ml;
    adding into said matrix bilirubin dissolved in 0.1M NaOH so as to obtain between about 1 and 30 mg/dl of bilirubin in a bilirubin containing matrix, said dissolved bilirubin being substantially clear; and
    sealing said bilirubin containing matrix in a reclosable, air tight container.

5. A stabilized aqueous bilirubin calibrator solution comprising:
    between about 1.0 and 30 mg/dl bilirubin;
    bistrispropane at about 0.1M;
    between about 0.1 and 0.53 weight percent gluconic acid generated in situ from glucose;
    between about 4 to about 6 weight percent albumin;
    d-lactate hydrogen donor at between about 3 and 20 mM; and
    between about 0.3 and 0.6 units/ml sterile membrane fragments derived from bacteria having membranes containing an oxygen transfer system which reduces oxygen to water;
    wherein said stabilized bilirubin calibrator solution has a pH from about 7.7 to about 7.8 and has a storage stability of at least six months at from about 2° to about 8° C. and at least four days at about 45° C., said calibrator solution further having an open vial stability of at least three weeks at from about 2° to about 8° C.

6. The bilirubin calibrator solution of claim 5 which further comprises up to about 0.024 weight percent butylated hydroxy toluene, from about 0.95 to about 1.0 weight percent ethanol, and from about 5 to about 6.4 weight percent polyoxyethylene 23 lauryl ether.

7. A stabilized aqueous bilirubin calibrator solution comprising:
    between about 1.0 and 30 mg/dl bilirubin;
    between about 0.1 and 0.53 weight percent gluconic acid generated in situ from glucose;
    between about 1 and 10 percent albumin;

between 0.3 and 0.6 units/ml sterile membrane fragments derived from bacteria having membranes containing an oxygen transfer system which reduces oxygen to water; and a substrate for said oxygen transfer system;

wherein said stabilized bilirubin calibrator solution has a pH from about 7.4 to about 8.1 and has a storage stability of at least six months at from about 2° to about 8° C. and at least four days at about 45° C., said calibrator solution further having an open vial stability of at least three weeks at from about 2° to about 8° C.

8. The bilirubin calibrator solution of claim 7 which further comprises catalase.

9. The bilirubin calibrator solution of claim 8 wherein the catalase is present in an amount up to about 150 units/ml.

10. The stabilized calibrator solution of claim 7 sealed in a reclosable, airtight container.

11. A method for stabilizing an aqueous bilirubin calibrator solution comprising:

preparing a matrix containing:

between about 0.1 and 0.53 weight percent glucose;

a substrate for an oxygen transfer system which reduces oxygen to water at between about 5 and 30 mM; and between about 1 and 10 weight percent albumin;

adjusting the pH of the matrix to from about 7.4 to about 8.1;

adding into the matrix sterile membrane fragments derived from bacteria having membranes containing said oxygen transfer system so as to obtain between about 0.3 and 0.6 units/ml of activity and thereafter excluding air from contacting said matrix;

after oxygen is removed from said matrix by the oxygen transfer system, adding into said matrix glucose oxidase so as to obtain from about 10 to 27 units/ml; and adding into said matrix bilirubin dissolved in 0.1M NaOH so as to obtain between about 1 and 30 mg/dl of bilirubin said dissolved bilirubin being substantially clear.

12. The method of claim 11 wherein the matrix obtained after the addition of bilirubin is sealed in a reclosable, airtight container.

* * * * *